United States Patent [19]

Laganà et al.

[11] 4,138,434
[45] Feb. 6, 1979

[54] INTEGRATED AMMONIA-UREA PRODUCING PROCESS, FOR THE PRODUCTION OF UREA

[75] Inventors: Vincenzo Laganà, Milan; Francesco Saviano, Segrate (Milan), both of Italy

[73] Assignee: Snamprogetti S.p.A., Milan, Italy

[21] Appl. No.: 857,185

[22] Filed: Dec. 2, 1977

[30] Foreign Application Priority Data

Dec. 23, 1976 [IT] Italy .................. 30797 A/76

[51] Int. Cl.² .......................... C07C 126/02
[52] U.S. Cl. .................... 260/555 A; 423/359
[58] Field of Search ............ 260/555 A; 423/359

[56] References Cited

U.S. PATENT DOCUMENTS

| | | | |
|---|---|---|---|
| 3,120,563 | 2/1964 | Bongaro | 260/555 A |
| 3,193,353 | 7/1965 | Matile et al. | 260/555 A |
| 3,607,939 | 9/1971 | Kaasenbrood et al. | 260/555 A |
| 3,674,847 | 7/1972 | Kaasenbrood et al. | 260/555 A |
| 3,711,544 | 1/1973 | Summerville | 260/555 A |
| 3,876,696 | 4/1975 | Guadalupi et al. | 260/555 A |
| 3,936,500 | 2/1976 | Kaasenbrood et al. | 260/555 A |
| 3,954,861 | 5/1976 | Guadalupi et al. | 260/555 A |
| 4,012,443 | 3/1977 | Bonetti | 260/555 A |

*Primary Examiner*—O. R. Vertiz
*Assistant Examiner*—Thomas W. Roy
*Attorney, Agent, or Firm*—Morgan, Finnegan, Pine, Foley & Lee

[57] ABSTRACT

An improvement of the SNAM ammonia-stripper integrated urea process is disclosed, wherein a gaseous stream obtained by decomposing hydrocarbons is fed to an adiabatic ammonia stripper placed downstream of a carbamate decomposer, the adiabatic stripper also receiving a solution of urea which is rich in ammonia coming from the carbamate decomposer. The thus enriched gaseous stream ($NH_3$, $CO_2$, $H_2O$) is processed in a $CO_2$-absorber (or carbamate reactor) and the process proceeds in the urea synthesis reactor. Recycling and recovery loops are provided between the several reaction and/or decomposing units. Surprisingly, enough, the stripping on $NH_3$ and $CO_2$ takes place adiabatically and the drop of the $CO_2$ partial pressure in the stream fed to the carbamate reactor has no bearing on the efficiency of the carbamate conversion which, according to the current technical teachings, requires an increase of the $CO_2$ partial pressure.

4 Claims, 1 Drawing Figure

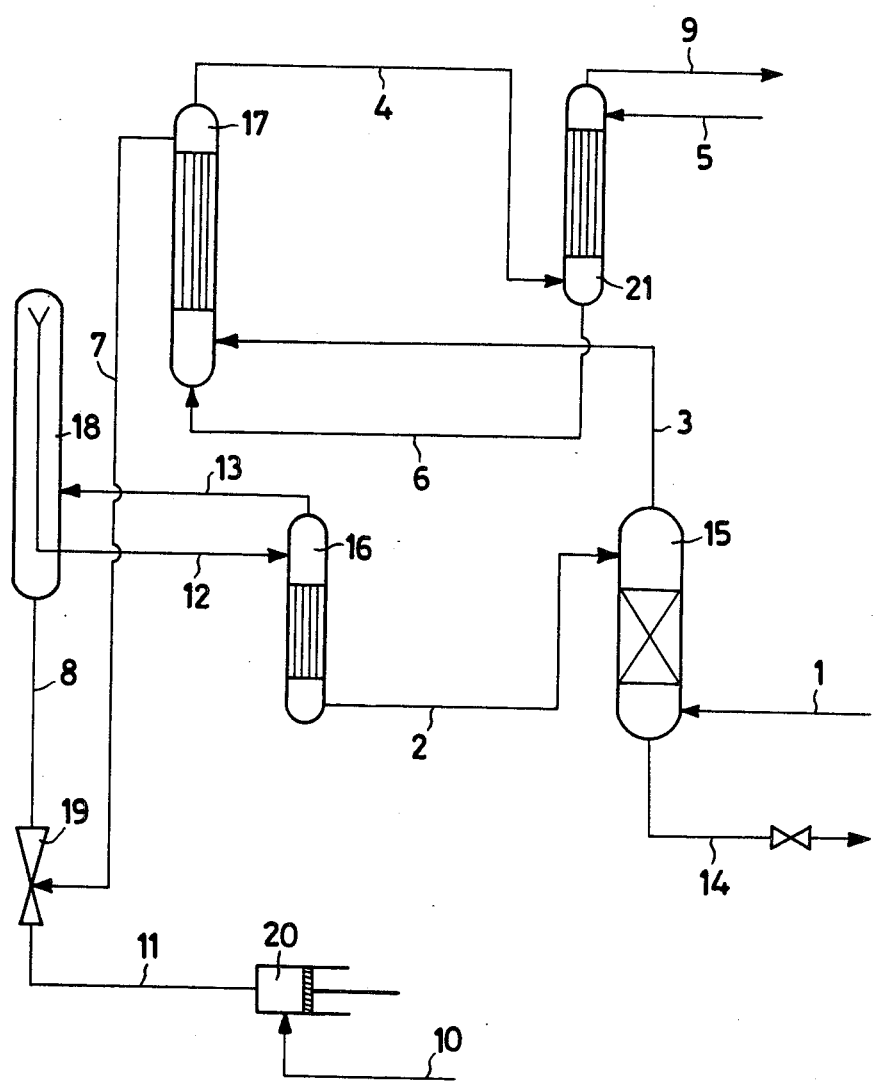

INTEGRATED AMMONIA-UREA PRODUCING PROCESS, FOR THE PRODUCTION OF UREA

This invention relates to an integrated ammonia-urea process for the production of urea.

Integrated processes for the production of ammonia and urea are known, and among these, more particularly, the one which is disclosed by the Italian Pat. No. 907,469.

Having reference to the latter patent, the ammonia-urea integrated process is performed by using the aqueous solution of ammonia as obtained by absorbing with water the ammonia emerging from the ammonia synthesizing reactor, to form ammonium carbamate by absorbing carbon dioxide as contained in the raw gases of the ammonia synthesis in a carbamate reactor.

The thusly formed carbamate is subsequently forwarded to a reactor for the synthesis of urea, wherefrom an aqueous solution of ammonium carbamate and urea is dumped, the carbamate being then decomposed into its components in a carbamate decomposer, from which such decomposition products are stripped with gaseous ammonia, and the decomposition products along with the gaseous stripping ammonia being recycled in the gaseous phase to the urea synthesis reactor. The method outlined hereinabove has the considerable defect that the ammonia content in the solution emerging from the stripper-decomposer is very high (about 37%). This fact involves an oversizing and an exceedingly high consumption of steam for the ammonia recovery section downstream of the carbamate decomposer-stripper.

An object of the present invention is to provide an integrated method for the production of urea, which makes it possible to overcome the drawbacks of the integrated method indicated hereinabove.

The method which is the subject-matter of the present invention comprises the steps of feeding the gaseous stream as obtained from steam reforming or partial oxidation of liquid or gaseous hydrocarbons which compose the raw gas for the synthesis of ammonia, and which is principally composed by $CO_2$, $H_2$ and $N_2$, to a stripping column in counterflow relationship relatively to the ammonia-enriched solution which comes from the carbamate decomposer.

The method according to the present invention, more particularly, comprises the step of feeding the gaseous stream obtained by steam-reforming of hydrocarbons and which forms the raw gas for the synthesis of ammonia and which is essentially composed by $CO_2$, $H_2$ and $N_2$, to an adiabatic stripping column positioned downstream of a carbamate decomposer, said column being fed with the ammonia-enriched urea solution coming from such carbamate decomposer.

The above indicated gaseous stream enriched with $NH_3$, $H_2O$ and $CO_2$ passes from the adiabatic stripper to a $CO_2$-absorbing column, wherein there is used as the absorbing liquor an aqueous solution of ammonium carbonate enriched with ammonia and which is obtained by washing in a column the gaseous non absorbed stream rich with ammonia and containing substantially $N_2$ and $H_2$ coming from the $CO_2$-absorbing column aforesaid, along with an aqueous solution of ammonium carbonate coming from the low-pressure section of the urea plant.

The gases which have not been absorbed in the absorption column of the stream, such gases coming from the $CO_2$-absorber, and essentially composed by $N_2$ and $H_2$ and traces of CO and $CO_2$, are sent to methanization and then to the ammonia synthesis.

The solution of ammonium carbamate as formed in the $CO_2$-absorption column, is sent to the urea synthesis reactor, preferably via an ejector or another static system, by exploiting the pressure power of the anhydrous ammonia and/or of the ammonia in aqueous solution as fed through said ejector or another static system to the urea-synthesis reactor.

In the urea-synthesizing reactor the dehydration of the carbamate to urea is completed and a solution of urea is obtained which is rich with ammonium carbamate, said solution being then sent to a carbamate decomposer wherein about 50% of such carbamate is decomposed into $CO_2$ and $NH_3$, said ammonia and carbon dioxide being directly recycled in the gaseous state without any previous condensations, to the urea-synthesizing reactor, whereas the solution of urea emerging from the decomposer is sent to the stripper.

It has been found that the ammonia stripping operation by the gaseous stream can be effected adiabatically without any administration of heat, inasmuch as the heat contained in the solution to be treated is such that the solution supplies the heat necessary to stripping when cooled.

Along with ammonia, also the residual $CO_2$ is stripped together with a certain amount of water as contained in the solution coming from the carbamate decomposer.

The gas which has been enriched with ammonia, water, carbon dioxide, is sent to the $CO_2$-absorber, wherein the $CO_2$ is absorbed by an aqueous solution of ammonium carbonate which is rich with ammonia.

In the $CO_2$-absorbing device (i.e. the carbamate reactor), ammonium carbamate is formed, which is sent, as outlined above, to a urea-synthesizing reactor, wherefrom a urea solution is discharged, which is treated in a carbamate decomposer: in the latter, about 50% of the ammonium carbamate which has not been converted into urea is decomposed, whereafter the urea solution is stripped of its ammonia and residual $CO_2$ by a gas which is essentially composed of $CO_2$, $H_2$ and $N_2$, as described above.

When operating according to the method of this invention, it becomes thus possible to obtain a concentrated aqueous solution of urea which is ammonia-poor, which makes it possible to simplify considerably the $NH_3$-recovery section: the latter can now be composed of a single stage from 1 to 8 atmospheres, so that the intermediate 18-atmosphere stage, which is generally required, can be dispensed with.

An additional advantage of the method according to the present invention is the fact of obtaining, at the outlet of the ammonia condenser, a raw gas from the ammonia synthesis, which is exempt from $CO_2$ and which has an extremely low contents of gaseous ammonia (about 2%) by virtue of the use, as the absorbing means, of the ammonia contained in the aqueous solution of carbonate coming from the section of recovery of the urea plant. The reduction of the ammonia contents (about 14% in the cited patent) involves a higher efficiency of the methanization section which serves to remove the traces of CO and $CO_2$ contained in the ammonia synthesis raw gas.

It is important to emphasize the fact that the urea-synthesis reactor, the carbamate decomposer, the adiabatic stripping column, the $CO_2$-absorber and the ammonia condenser are operated substantially under the same pressure as the urea-synthesis reactor, less the pressure drops in the loop. Such a pressure is within the range of from 100 to 250 atmospheres. The carbamate formation heat which is evolved in the carbamate reactor is used for producing steam which is used in the urea-concentration sections.

It is apparent from the foregoing that the combined cycle (thermal stripping for the decomposition of carbamate and adiabatic stripping for removing ammonia and residual $CO_2$) affords a considerable degree of cheapness and simplicity.

The integrated method according to the present invention will now be illustrated without limitation by the aid of the diagram of the accompanying drawing.

BRIEF DESCRIPTION OF THE DRAWING

The FIGURE is a diagrammatic illustration of apparatus adapted for use in the practice of our invention.

The raw gas as obtained by steam-reforming of hydrocarbons in a conventional manner, which is mainly composed of $CO_2$, $N_2$ and $H_2$, is sent after having been compressed and through the piping 1, to an adiabatic ammonia-stripper 15 intended to remove the ammonia contained in the solution which comes, via the pipe 2, from the carbamate decomposer 16.

The gases, which have been more or less enriched with ammonia, are sent, via the duct 3, to the $CO_2$-absorber, 17, and at the outlet of 17, they are sent, via the duct 4, to the ammonia-condenser 21: the latter is fed, via the pipe 5, with an aqueous solution of ammonium carbonate coming from the carbamate- and ammonia-recovery section of the urea plant.

In the $CO_2$-absorber 17, the carbon dioxide reacts nearly completely with the ammonia contained in the ammoniacal solution which is fed via 6 to form a solution of ammonium carbamate: the latter is discharged through the duct 7 and is fed to the urea-synthesizing reactor 18 through the ejector 19 and the line 8.

The portion of $CO_2$ which did not react in the absorber 17 issues from the head of the absorber together with the ammonia synthesis gas via the line 4 and is absorbed by a solution of ammonium carbonate rich in ammonia in the absorber 21 which works substantially as an ammonia condenser, to form a solution of ammonium carbamate which is discharged and introduced via 6 into the bottom section of the absorber 17.

The ammonia-synthesis gases, deprived of $CO_2$ and $NH_3$, which emerge from the apparatus 21 via the line 9, are fed to a methanization apparatus, to be forwarded subsequently to an ammonia-synthesizing reactor in which ammonia is produced. This ammonia is washed away from the unreacted gases with water, the resultant aqueous solution of ammonia being sent via the line 10 to the urea-synthesizing reactor 18.

The solution of carbamate admixed in the ejector 19 with the ammoniacal solution coming, through the line 10, from the ammonia synthesis section, enters the urea-synthesizing reactor 18 to start the carbamate-dehydration reaction and the consequential formation of the urea.

The ammoniacal solution is pumped by the pump 20, via the line 11, to the ejector 19, the latter delivering to the carbamate solution coming from 17 the power which is sufficient to have such a solution enter the urea reactor 18 through the line 8.

The solution of urea which has been formed in the reactor 18, enters, through the line 12, the carbamate decomposer 16, wherein by the administration of heat about 50% of the unconverted carbamate is decomposed and the products of such a decomposition, which are essentially composed of $NH_3$, $CO_2$ and $H_2O$ are recycled to the reactor 18 via the line 13.

The solution of urea enriched with ammonia is fed, via the piping 2, to the adiabatic stripper 15, as disclosed hereinabove.

It is quite surprising that, when working with the method according to this invention, the stripping of the ammonia and the carbon dioxide contained in the solution can take place adiabatically without any administration of heat, and that the decrease of the $CO_2$-partial pressure in the stream sent to the carbamate reactor, with respect to the case in which the raw gases is not passed through the adiabatic stripper but is directly sent to the carbamate reactor, has no bearing on the conversion to carbamate: this is in complete contradiction to the teachings of the conventional art, according to which the pressure of $CO_2$ must be increased in order that the conversion to carbamate may be increased.

A modification which has not been shown in the drawing, but which could have a considerable importance in the case in which there is an ammonia synthesis section operated under a pressure which exceeds by 10 to 400 atmosphere the pressure of the isobaric urea-synthesizing loop, consists in dispensing with the pumping of the ammoniacal solution by the pump 20 and in compressing, conversely, the gases of the line 9 up to the pressure which obtains in the ammonia-synthesizing are, the result being the obtainment of anhydrous and-/or aqueous ammonia, which can be directly sent, without being additionally pumped, to the ejector 19.

As regards the pressures, the method according to the present invention can be either isobaric, or nonisobaric. In the former case, the pressures range from 100 to 300 kgs/sq.cm, whereas in the latter case, more particularly, the urea-production section can be operated under a pressure which, as outlined above, can be from 10 to 400 atmospheres less than the ammonia synthesis pressures.

A example will now be given, which is intended better to illustrate the invention without limiting the scope thereof in any way.

EXAMPLE

The stating data are:
Raw material — $CH_4$
Required production — 1,000 metric tons daily of prilled urea 16,362 Normal cubic meters hourly, of a natural gas considered as 100% methane, are converted, according to the conventional techniques, such as primary reforming, secondary reforming, conversion of CO at high and low temperature, into a mixture of converted gas having the following composition, on a dry basis:

| Rate of flow | 88,297 | normal cubic meters hourly | Pressure 32 atm. | |
|---|---|---|---|---|
| $H_2$ | 54,120 | " | 61.50% | by volume |
| $N_2$ | 17,600 | " | 20.00% | " |
| CO | 370 | " | 0.42% | " |
| $CO_2$ | 15,565 | (30,572 kg) | 17.35% | " |
| A | 211 | " | 0.24% | " |
| $CH_4$ | 431 | " | 0.49% | " |

The gas is compressed up to 200 kgs/sq.cm at a temperature of 145° C. and sent firstly to the adiabatic stripper 15, then, for the absorption of $CO_2$, to the absorber 17 and to the ammonia condenser 21, and finally to the methanization through the line 9. The gas, at the temperature of about 190° C., emerging from the stripping column 15 has the following composition (stripped substances included):

| | | | | |
|---|---|---|---|---|
| $H_2$ | 54,120 | nor. cu. meter/hourly | 34.94% | by volume |
| $N_2$ | 17,600 | " | 11.36% | " |
| CO | 370 | " | 0.24% | " |
| $CO_2$ | 19,012 | (37,322 kgs) | 12.27% | " |
| A | 211 | nor. cu. meter/hourly | 0.14% | " |
| $CH_4$ | 431 | " | 0.28% | " |
| $NH_3$ | 54,024 | (41,642 kgs) | 34.88% | " |
| $H_2O$ | 9,124 | ( 7,336 kgs) | 5.89% | " |
| | 154,892 | nor. cu. meter/hourly, | Total rate of flow | |

The gas enters the $CO_2$-absorber 17 through the duct 3, and meets, in the absorber, the absorbing solution having a temperature of 50° C. and the following composition and rate of flow:

| | | | | |
|---|---|---|---|---|
| $NH_3$ | 25,511 | kilograms/hour | 71.43% | by weight |
| $CO_2$ | 4,916 | " | 13.76% | " |
| $H_2O$ | 5,287 | " | 14.81% | " |
| | 35,714 | " | Total rate of flow | |

The carbamate dumped through 7 and recycled to the reactor 18 via the ejector 19 has the following composition and rate of flow at a temperature of 155° C.:

| | | | | |
|---|---|---|---|---|
| $NH_3$ | 44,653 | kgs/hourly | 47.23% | by weight |
| $CO_2$ | 38,588 | " | 40.81% | " |
| $H_2O$ | 11,303 | " | 11.96% | " |
| | 94,544 | " | Total rate of flow | |

The gas issuing from the $CO_2$-absorber 17 enters the $NH_3$-condenser 21 via the line 4 and has the following composition at a temperature of 155° C.:

| | | | | |
|---|---|---|---|---|
| $H_2$ | 54,120 | normal cu. meters/hourly | 51.32% | by volume |
| $N_2$ | 17,600 | " | 16.69% | " |
| CO | 370 | " | 0.35% | " |
| $CO_2$ | 1,859 | "( 3,650 kgs) | 1.76% | " |
| A | 211 | " | 0.20% | " |
| $CH_4$ | 431 | " | 0.41% | " |
| $NH_3$ | 29,220 | "(22,500 kgs) | 17.71% | " |
| $H_2O$ | 1,642 | "( 1,320 kgs) | 1.56% | " |
| | 105,454 | " | Total rate of flow | |

In the ammonia condenser, the gas meets in counterflow relationship the carbonate soution, 5, at the temperature of 40° C., which has the following rates of flow and composition:

| | | | | |
|---|---|---|---|---|
| $NH_3$ | 4,167 | kgs hourly | 43% | by weight |
| $CO_2$ | 1,282 | " | 13% | " |
| $H_2O$ | 4,242 | " | 44% | " |
| | 9,691 | " | Total rate of flow | |

The gas is properly purified to be sent to the methanization section via the line 9 and has the following composition and rates of flow at a temperature of 40° C.:

| | | | | |
|---|---|---|---|---|
| $H_2$ | 54,120 | nor. cu. meters hourly | 72.56% | by volume |
| $N_2$ | 17,600 | " | 23.60% | " |
| CO | 370 | " | 0.50% | " |
| $CO_2$ | 8 | "(16 kgs/hr) | 0.01% | " |
| A | 211 | " | 0.28% | " |
| $CH_4$ | 431 | " | 0.58% | " |
| $NH_3$ | 1,500 | " | 2.01% | " |

-continued

| | | | | |
|---|---|---|---|---|
| $H_2O$ | 342 | " | 0.46% | " |
| | 74,582 | " | Total rate of flow | |

The carbamate, through the line 7 and through the ejector 19 is admixed with the following ammoniacal solution (temperature 40° C.):

| | | | | |
|---|---|---|---|---|
| $NH_3$ | 24,767 | kgs/hr | 80.0% | by weight |
| $H_2O$ | 6,192 | " | 20.0% | " |
| | 30,959 | " | Total rate of flow | | and, through the line 8 the solution which forms the reaction mixture enters the reactor 18 at the temperature of 116° C.

The mixture has the following composition:

| | | | | |
|---|---|---|---|---|
| $NH_3$ | 69,420 | kgs hourly | 55.31% | by weight |
| $CO_2$ | 38,588 | " | 30.75% | " |
| $H_2O$ | 17,495 | " | 13.94% | " |
| | 125,503 | " | Total rate of flow | |

From the reactor 18 a solution emerges which has the following composition at a temperature of 186° C.:

| | | | | |
|---|---|---|---|---|
| $NH_3$ | 70,513 | kgs hourly | 44% | by weight |
| $CO_2$ | 16,026 | " | 10% | " |
| Urea | 41,667 | " | 26% | " |
| $H_2O$ | 32,052 | " | 20% | " |
| | 160,258 | " | Total rate of flow | |

Through the line 12 the carbamate decomposer 16 is fed, wherefrom the treated solution 2 emerges (temperature 208° C.).

| | | | | |
|---|---|---|---|---|
| $NH_3$ | 45,809 | kgs hourly | 36.50% | by weight |
| $CO_2$ | 8,032 | " | 6.40% | " |
| Urea | 41,667 | " | 33.20% | " |
| $H_2O$ | 29,995 | " | 23.90% | " |
| | 125,503 | " | Total rate of flow | |

The stripped gases enter, through the line 13, the reactor 18 (temperature 195° C.).

| | | | | |
|---|---|---|---|---|
| $NH_3$ | 24,704 | kgs hourly | 71.08% | by weight |
| $CO_2$ | 7,994 | " | 23.00% | " |
| $H_2O$ | 2,057 | " | 5.92% | " |
| | 34,755 | " | Total rate of flow | |

The solution of urea emerging from the carbamate decomposer 16 is fed, via the line 2, to the adiabatic stripper 15 wherein according to the present invention, it meets in counterflow relationship the raw gas 1 and is purified until the following composition is obtained:

| | | | | |
|---|---|---|---|---|
| $NH_3$ | 4,167 | kgs hourly | 6.5% | by weight |
| $CO_2$ | 1,282 | " | 2.0% | " |
| $CO_2$ | 1,282 | " | 2.0% | " |
| Urea | 41,667 | " | 65.0% | " |
| $H_2O$ | 22,659 | " | 26.5% | " |
| | 69,775 | " | Total rate of flow | |

The solution thus obtained at the temperature of 90° C. approx. is discharged via the line 14, to the recovery section for ammonia and carbon dioxide at low pressure according to the usual procedure.

In the carbamate reactor 17, there is used the heat of formation of the carbamate itself for producing saturated steam at a pressure of 4.5 atm corresponding to a hourly rate of flow of about 30,000 kilograms.

We claim:

1. An integrated process for the production of urea which comprises carrying out in a urea synthesis section the steps of:
    (a) feeding a stream of anhydrous ammonia and/or ammonia in aqueous solution and a stream containing ammonium carbamate to a urea-synthesizing reactor so that urea is synthesized therein;
    (b) withdrawing a solution of urea containing ammonium carbamate from the urea-synthesizing reactor and feeding said stream to a decomposer wherein about 50% of said ammonium carbamate is decomposed providing ammonia and carbon dioxide;
    (c) recycling gaseous ammonia and carbon dioxide from said decomposer to the urea-synthesizing reactor;
    (d) withdrawing a solution of urea containing the balance of said ammonium carbamate and enriched with ammonia from said decomposer;
    (e) feeding said solution withdrawn from the decomposer in step (d) to an adiabatic stripping column;
    (f) feeding a stream of stripping gas consisting of raw ammonia synthesis gases and composed essentially of $CO_2$, $N_2$ and $H_2$ to said stripping column whereby said urea solution is purified and said stripping gas stream is enriched with $NH_3$, $H_2O$ and $CO_2$;
    (g) recovering purified urea solution from said stripping column;
    (h) feeding said enriched stripping gas stream from the stripping column to a $CO_2$ absorber;
    (i) feeding an absorbing liquid comprised of an ammoniacal aqueous solution of ammonium carbonate from an ammonia condenser to the $CO_2$ absorber so that ammonium carbamate solution is formed in said absorber;
    (j) withdrawing ammonium carbamate solution from the $CO_2$ absorber to provide said stream containing ammonium carbamate fed to said urea synthesizing reactor in step (a);
    (k) feeding a stream of non-absorbed synthesis gas rich with ammonia and containing $N_2$ and $H_2$ from the $CO_2$ absorbing column to said ammonia condenser;
    (l) feeding an aqueous solution of ammonium carbonate to the ammonia condenser so that the aqueous solution of ammonium carbonate fed to the $CO_2$ absorber in step (i) is produced; and
    (m) recovering $N_2$ and $H_2$ from said ammonia condenser for transmission to an ammonia synthesis section.

2. A process as claimed in claim 1, wherein the solution of ammonium carbamate is fed to the urea synthesizing reactor in step (a) through an ejector in which the motive fluid is the anhydrous ammonia or the aqueous solution of ammonia fed to the urea-synthesizing reactor in said step.

3. A process as claimed in claim 1, wherein the pressure is in the range between 100 and 300 atmospheres.

4. A process as claimed in claim 1, wherein the pressure in the ammonia synthesis section exceeds by from 10 to 400 atmospheres the pressure in the urea-synthesis section.

* * * * *

UNITED STATES PATENT AND TRADEMARK OFFICE
CERTIFICATE OF CORRECTION

PATENT NO. : 4,138,434                                Page 1 of 2

DATED : February 6, 1979

INVENTOR(S) : Vincenzo Lagana and Francesco Saviano

It is certified that error appears in the above-identified patent and that said Letters Patent are hereby corrected as shown below:

First page, line 12, of the Abstract, after "surprisingly" delete the comma ",".

Col. 3, line 29, after "and" insert a comma --,--.

Col. 4, line 31, correct "are" to read --area--.

Col. 5, first composition, line beginning with "$NH_3$" insert ditto marks --"-- before "(41,642 kgs)"; and in line beginning with "$H_2O$" insert ditto marks --"-- before "(7,336 kgs)".

UNITED STATES PATENT AND TRADEMARK OFFICE
CERTIFICATE OF CORRECTION

PATENT NO. : 4,138,434
DATED : February 6, 1979
INVENTOR(S) : Vincenzo Lagana and Francesco Saviano It is certified that error appears in the above-identified patent and that said Letters Patent are hereby corrected as shown below:

Col. 6, lines 41 and 42, correct the figures "29,995" to read --29,995--;

line 60, delete the second occurrence of the line beginning with "$CO_2$".

Signed and Sealed this

Twenty-fifth Day of September 1979

[SEAL]

Attest:

Attesting Officer

LUTRELLE F. PARKER
Acting Commissioner of Patents and Trademarks